US00PP20656P2

(12) United States Plant Patent
Verschoor

(10) Patent No.: US PP20,656 P2
(45) Date of Patent: Jan. 19, 2010

(54) ***ASTILBE* PLANT NAMED 'VERSSILVERY PINK'**

(50) Latin Name: ***Astilbe arendsii*×*Astilbe japonica***
Varietal Denomination: Verssilvery Pink

(76) Inventor: Jan Verschoor, Marcelisvaartpad 17, 2015 CS Haarlem (NL)

( * ) Notice: Subject to any disclaimer, the term of this patent is extended or adjusted under 35 U.S.C. 154(b) by 0 days.

(21) Appl. No.: 12/284,869

(22) Filed: Sep. 22, 2008

(51) Int. Cl.
*A01H 5/00* (2006.01)

(52) U.S. Cl. ..... Plt./407

(58) Field of Classification Search ..... Plt./407
See application file for complete search history.

*Primary Examiner*—June Hwu
(74) *Attorney, Agent, or Firm*—C. A. Whealy

(57) ABSTRACT

A new and distinct cultivar of *Astilbe* plant named 'Verssilvery Pink', characterized by its compact, upright and strong plant habit; strong and healthy foliage; freely and uniformly flowering habit; light pink-colored flowers; and good garden performance.

2 Drawing Sheets

Botanical designation: *Astilbe arendsii*×*Astilbe japonica*.
Cultivar denomination: 'Verssilvery Pink'.

BACKGROUND OF THE INVENTION

The present invention relates to a new and distinct cultivar of *Astilbe*, botanically known as *Astilbe arendsii*×*Astilbe japonica* and hereinafter referred to by the name 'Verssilvery Pink'.

The new *Astilbe* plant is a product of a planned breeding program conducted by the Inventor in Haarlem, The Netherlands. The objective of the breeding program was to create new strong *Astilbe* cultivars with attractive foliage and flower coloration.

The new *Astilbe* plant originated from a cross-pollination made by the Inventor in 2001 in Haarlem, The Netherlands, of an unnamed *Astilbe arendsii* seedling selection, not patented, as the female, or seed, parent with an unnamed *Astilbe japonica* seedling selection, not patented, as the male, or pollen, parent. The new *Astilbe* was discovered and selected by the Inventor as a single flowering plant within the progeny of the stated cross-pollination in a controlled greenhouse environment in Haarlem, The Netherlands in 2003.

Asexual reproduction of the new *Astilbe* plant by divisions in a controlled environment in Honselersdijk, The Netherlands since the summer of 2003, has shown that the unique features of this new *Astilbe* plant are stable and reproduced true to type in successive generations.

SUMMARY OF THE INVENTION

Plants of the new *Astilbe* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Verssilvery Pink'. These characteristics in combination distinguish 'Verssilvery Pink' as a new and distinct cultivar of *Astilbe:*

1. Compact, upright and strong plant habit.
2. Strong and healthy foliage.
3. Freely and uniformly flowering habit.

4. Cerise-colored flowers.
5. Good garden performance.

Plants of the new *Astilbe* differ primarily from plants of the parent selections in plant height and flowering habit as plants of the new *Astilbe* are more compact and more freely flowering than plants of the parent selections.

Plants of the new *Astilbe* can be compared to plants of *Astilbe arendsii* 'Europa', not patented. In side-by-side comparisons conducted in Haarlem, The Netherlands, plants of the new *Astilbe* and the cultivar Europa differed in the following characteristics:

1. Plants of the new *Astilbe* were more compact than plants of 'Europa'.
2. Plants of the new *Astilbe* were more freely flowering than plants of 'Europa'.
3. Flowers of plants of the new *Astilbe* were darker in color than flowers of plants of 'Europa'.

BRIEF DESCRIPTION OF THE PHOTOGRAPHS

The accompanying colored photographs illustrate the overall appearance of the new *Astilbe*, showing the colors as true as it is reasonably possible to obtain in colored reproductions of this type. Colors in the photographs may differ slightly from the color values cited in the detailed botanical description which accurately describe the colors of the new *Astilbe.*

The photograph on the first sheet comprises a side perspective view of a typical flowering plant of 'Verssilvery Pink' grown in a container.

The photograph at the top of the second sheet is a close-up view of typical inflorescences of 'Verssilvery Pink'.

The photograph at the bottom of the second sheet is a close-up view of the upper surface of a typical leaf of 'Verssilvery Pink'.

DETAILED BOTANICAL DESCRIPTION

The aforementioned photographs and following observations, measurements and values describe plants grown in containers in Afferden, The Netherlands, under commercial practice in during the early summer in an outdoor nursery with day temperatures ranging from 12° C. to 27° C. and night temperatures ranging from 4° C. to 16° C. Plants had been growing for two years when the photographs and description were taken. In the following description, color references are made to The Royal Horticultural Society Colour Chart, 2001 Edition, except where general terms of ordinary dictionary significance are used.

Botanical classification: *Astilbe arendsii*×*Astilbe japonica* 'Verssilvery Pink'.

Parentage:

*Female, or seed, parent.*—Unnamed *Astilbe arendsii* seedling selection, not patented.

*Male, or pollen, parent.*—Unnamed *Astilbe japonica* seedling selection, not patented.

Propagation:

*Type.*—By divisions.

*Time to initiate roots.*—About three weeks at 20° C.

*Root description.*—Thick, fleshy; brown in color.

*Rooting habit.*—Freely branching; dense.

Plant description:

*Plant form/habit.*—Herbaceous perennial. Compact, upright and strong plant habit; roughly triangular. Flowering stems and leaves basal; dense and bushy growth habit; moderate to low vigor. Freely and uniformly flowering with numerous flowers on branched panicles.

*Growth rate.*—Moderate to slow; from divisions, about 28 weeks are required to produce fully-grown flowering plants.

*Plant height* (*soil level to top of foliar plane*).—About 22.5 cm.

*Plant height* (*soil level to top of inflorescences*).—About 34.6 cm.

*Plant width* (*spread*).—About 30.1 cm.

*Stem description.*—Length: About 13.4 cm. Diameter: About 2.5 mm. Internode length: About 4.3 cm. Strength: Strong. Texture: Smooth, glabrous. Color: Close to 152A.

Foliage description:

*Arrangement.*—Alternate; biternately compound.

*Leaf length* (*excluding petiole*).—About 9.6 cm.

*Leaf width.*—About 8.2 cm.

*Lateral leaflet length.*—About 3.1 cm.

*Lateral leaflet width.*—About 1.4 cm.

*Terminal leaflet length.*—About 3.7 cm.

*Terminal leaflet width.*—About 1.4 cm.

*Lateral and terminal leaflet shape.*—Elliptic.

*Lateral and terminal leaflet apex.*—Acute.

*Lateral and terminal leaflet base.*—Rounded.

*Lateral and terminal leaflet margin.*—Biserrate.

*Lateral and terminal leaflet texture, upper surface.*—Smooth, glabrous.

*Lateral and terminal leaflet texture, lower surface.*—Sparsely pubescent; slightly rough.

*Lateral and terminal leaflet venation pattern.*—Pinnate.

*Lateral and terminal leaflet color.*—Developing leaves, upper surface: Close to 143B. Developing leaves, lower surface: Close to 143C. Fully expanded leaves, upper surface: Between 137A and 141A; venation, close to 144C. Fully expanded leaves, lower surface: Close to 137C; venation, close to 148C.

*Leaf petiole length.*—About 5.4 cm.

*Leaf petiole diameter.*—About 1.5 mm.

*Leaflet petiole length.*—About 1.6 cm.

*Leaflet petiole width.*—About 1.5 mm.

*Leaf and leaflet petiole texture, upper and lower surfaces.*—Smooth, glabrous.

*Leaf and leaflet petiole color, upper and lower surfaces.*—Between 144B to 144C and 148A; at the nodes, close to 187C.

Flower description:

*Flower type/habit.*—Numerous single rotate flowers arrange on terminal branched panicles; flowers fact upright, outward or downward depending on position on the panicle. Panicles conical in shape. Freely and uniformly flowering habit with about 1,000 flowers and flower buds per inflorescence.

*Fragrance.*—Moderately fragrant; sweet.

*Natural flowering season.*—Continuously flowering during the summer to late summer in The Netherlands.

*Postproduction longevity.*—Flowers last about ten days on the plant; flowers persistent.

*Flower buds.*—Height: About 2 mm. Diameter: About 1.5 mm. Shape: Ovoid. Color: Close to 62A to 62B; towards the base, close to 145B.

*Inflorescence height.*—About 21.5 cm.

*Inflorescence diameter.*—About 10.7 cm.

*Flower diameter.*—About 8 mm.

*Flower depth.*—About 4 mm.

*Petals.*—Quantity per flower: Typically five in a single whorl. Length: About 4 mm. Lobe width: About 1 mm. Shape: Narrowly oblanceolate. Apex: Obtuse. Margin: Entire. Texture, upper and lower surfaces: Smooth, glabrous. Color: Developing petals, upper surface: Close to 69A to 69B. Developing petals, lower surface: Close to 65A to 65B. Fully expanded petals, upper and lower surfaces: Close to 69B to 69C; color becoming close to 69D with development.

*Sepals.*—Quantity per flower: Typically five in a single whorl, fused towards the base; campanulate calyx. Length: About 2 mm. Width: About 1 mm. Shape: Ovate. Apex: Acute. Base: Cuneate. Margin: Entire. Texture, upper and lower surfaces: Smooth, glabrous. Color: Developing sepals, upper and lower surfaces: Close to 157A; towards the apex and margins, close to 186C. Fully expanded sepals, upper and lower surfaces: Close to N155B to N155C; towards the apex and margins, flushed with close to 65C.

*Peduncles.*—Length: About 20.8 cm. Diameter: About 2 mm. Angle: Erect. Strength: Strong. Texture: Smooth, glabrous. Color: Close to 150B.

*Pedicels.*—Length: About 2 mm. Diameter: About 0.5 mm. Angle: About 45° from vertical. Strength: Moderately strong. Texture: Smooth, glabrous. Color: Close to N155B to N155C.

*Reproductive organs.*—Stamens: Quantity per flower: Typically ten; anthers basifixed. Filament length: About 2 mm. Anther shape: Ovate. Anther length: About 0.3 mm. Anther color: Close to 155D. Pollen amount: Scarce. Pollen color: Close to N155A. Pistils: Quantity per flower: Two. Pistil length: About 1.8 mm. Stigma shape: Club-shaped. Stigma color: Close to 69D. Style length: About 1.5 mm. Style color: Close to 69C to 69D. Ovary color: Close to 69D.

*Seed/fruit.*—Seed and fruit development have not been observed.

Disease/pest resistance: Plants of the new *Astilbe* have not been noted to be resistant to pathogens and pests common to *Astilbe*.

Garden performance:

Plants of the new *Astilbe* have been observed to have good garden performance and tolerate rain, wind and high temperatures of about 35° C. Plants of the new *Astilbe* have been observed to be hardy to USDA Zone 5.

It is claimed:

1. A new and distinct *Astilbe* plant named 'Verssilvery Pink' as illustrated and described.

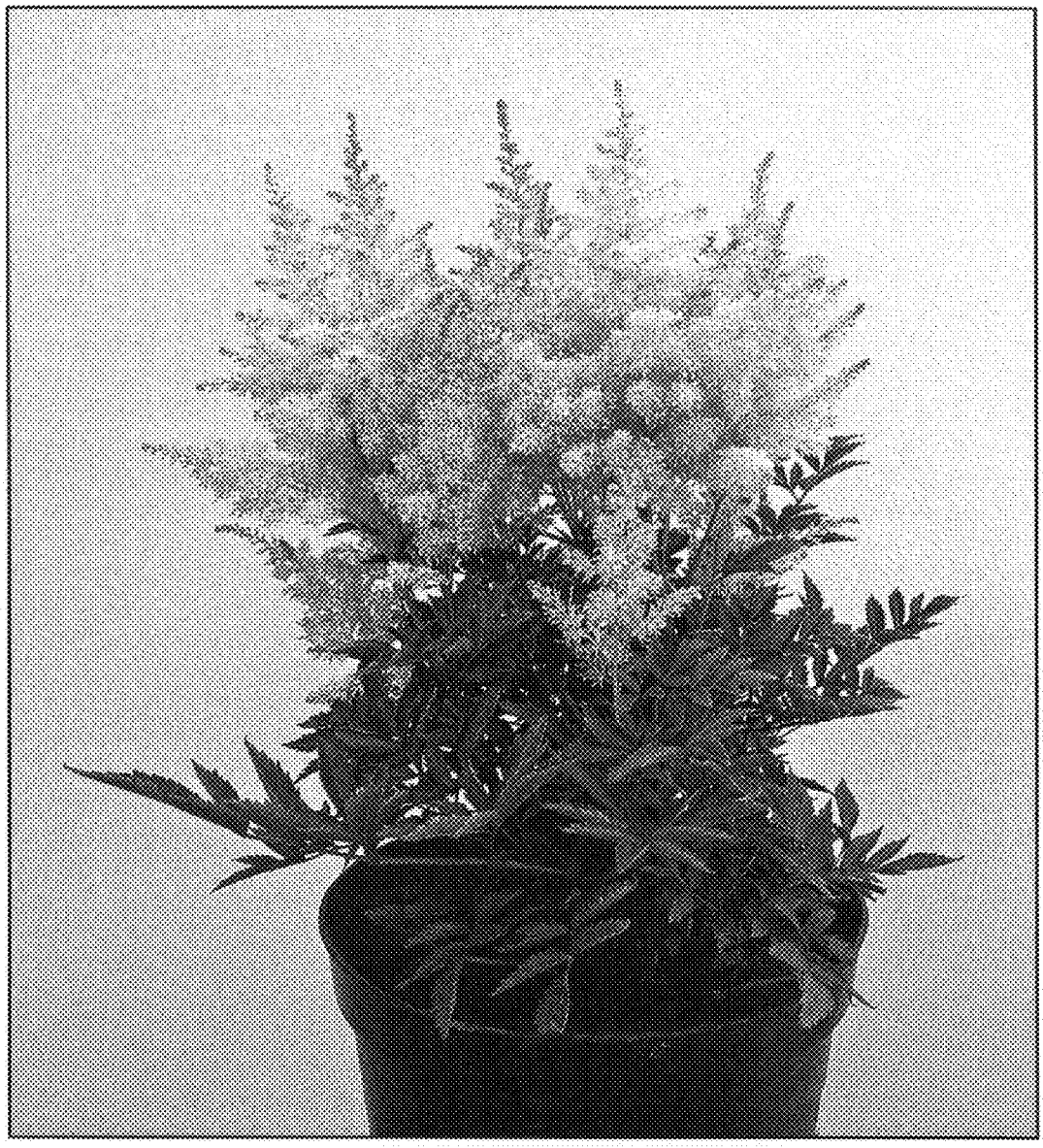

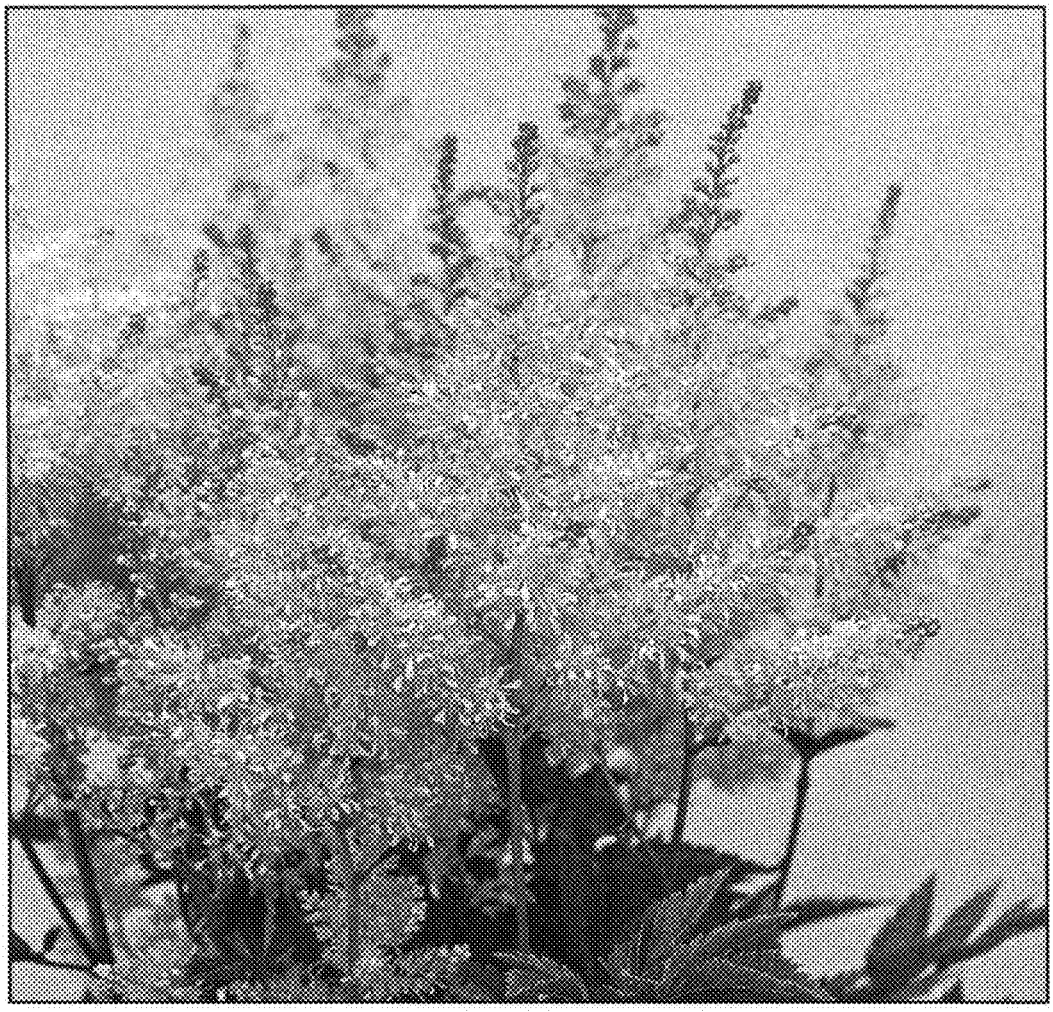
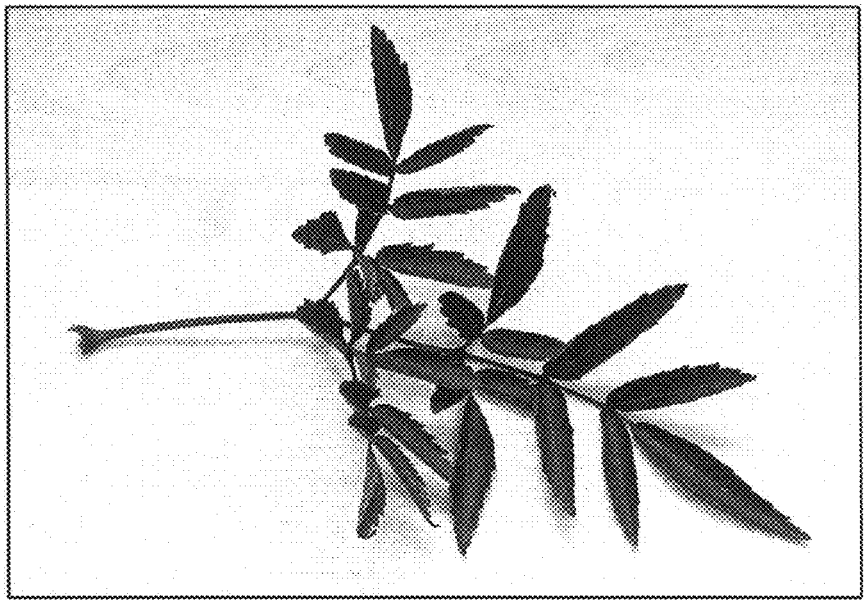

* * * * *